United States Patent [19]

Baglioni

[11] Patent Number: 4,487,771

[45] Date of Patent: Dec. 11, 1984

[54] C-3 SUBSTITUTED 1,4-BENZODIAZEPINES AND PHARMACEUTICAL UTILIZATION THEREOF

[75] Inventor: Alessandro Baglioni, Rome, Italy

[73] Assignee: Medosan Industrie Biochimiche Riunite, S.p.A., Albano Laziale, Italy

[21] Appl. No.: 591,408

[22] Filed: Mar. 20, 1984

[30] Foreign Application Priority Data

Mar. 23, 1983 [IT] Italy .............................. 47972 A/83

[51] Int. Cl.³ .................... A61K 31/55; C07D 243/24
[52] U.S. Cl. .............................. 424/244; 260/239.3 D
[58] Field of Search ................ 260/239.3 D; 424/244

[56] References Cited

U.S. PATENT DOCUMENTS

| | | | |
|---|---|---|---|
| 3,321,469 | 5/1967 | Walkenstein | 260/239.3 D |
| 3,520,877 | 7/1970 | Fryer et al. | 260/239.3 D |
| 3,801,568 | 4/1974 | Nudleman et al. | 260/239.3 D |
| 4,065,451 | 12/1977 | McCaully et al. | 260/239.3 D |

FOREIGN PATENT DOCUMENTS 2142181  3/1972  Fed. Rep. of Germany ... 260/239.3 D

Primary Examiner—Robert T. Bond
Attorney, Agent, or Firm—Cushman, Darby & Cushman

[57] ABSTRACT

New 3-substituted 1,4-benzodiazepine derivatives of general formula

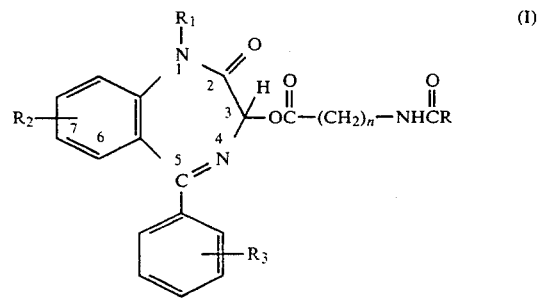

show useful and valuable pharmacological and therapeutic properties more specifically as anticonvulsants, antiepileptics, sedatives, hypnotics, muscle relaxants, analgesics, anxyolytics and tranquillizers.

17 Claims, No Drawings

C-3 SUBSTITUTED 1,4-BENZODIAZEPINES AND PHARMACEUTICAL UTILIZATION THEREOF

The present invention relates to new C-3 substituted 1,4-benzodiazepines and pharmaceutical utilisation thereof. More particularly it is concerned with N-substituted amino-acid esters of 3-hydroxy-1,4-benzodiazepine derivatives and their optically active isomers of formula

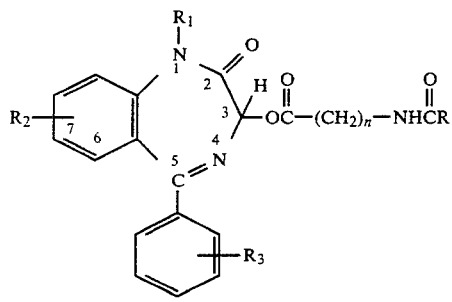

DESCRIPTION OF THE PRIOR ART

The 1,4-benzodiazepines represent a class of therapeutically active compounds which have found a large use in the treatment of various diseases of the central nervous system (Goodman and Gilman's The Pharmacological Basis of Therapeutics, 6th Edition, page 339, MacMillan, New York, N.Y. 1980).

Many substitutions in various positions of the ring system are known and used in human therapy. It is well known to those skilled in the art, that substitution of H by a halogen atom such as Cl, F, Br or even by $NO_2$, yields therapeutically active compounds. The same is true for substitution on the ortho position of the 5-phenylring, where H can be conveniently substituted by Cl, F, Br. It is also known that substitution of H on N in position 1 by $CH_3$ or even by $-CH_2CH_2N(C_2H_5)_2$ maintains the therapeutically useful properties of the parent compound. N in position 1 and the carbonyl group in position 2 can be bridged in such a way to form a triazol ring. Substitution on carbon in position 3 is also known in which H is substituted by OH. Esterification of this C3-hydroxy group has been achieved for example with trichloroacetic acid (T. Kovac et al., J. Med. Chem. 22, 1093 (1979)) but the high toxicity of the resulting esters prevents their use as therapeutic agents. These known esters (see also G. Maksay et al., J. Chromatography 174, 447 (1979) are not relevant to the compounds of the present invention, the peculiarity and novelty of which is characterized by the presence of suitably positioned, substituted nitrogen atom in the acyl portion of the ester.

SUMMARY OF THE INVENTION

In the general formula (I) of the invention, R represents a lower alkyl group up to 5 carbon atoms. R can also represent an alkoxy substituent with up to 4 carbon atoms. $R_1$ represents H, $CH_3$, $-CH_2CH_2N(C_2H_5)_2$. $R_2$ represents H, Cl, F, Br, trifluoromethyl, $NO_2$, the preferred position of $R_2$ being position 7 of the ring system. $R_3$ represents H, Cl, F, Br, the preferred position being the ortho position. n represents an integer number from 1 to 5, the preferred compounds being those with n equal to 3 corresponding to an N-substituted amino acid having the structure of the neurotransmitter GABA (γ-amino butyric acid) and those with n equal to 1, corresponding to an N-substituted amino acid having the structure of the neurotransmitter glycine.

The process by which the compounds of the invention are prepared consists in reacting an N-substituted amino acid of general formula (II) in the presence of an at least equivalent amount of suitable base in a suitable solvent and at a suitable temperature, with the C3—Cl derivative of a 1,4-benzodiazepine having general formula (III).

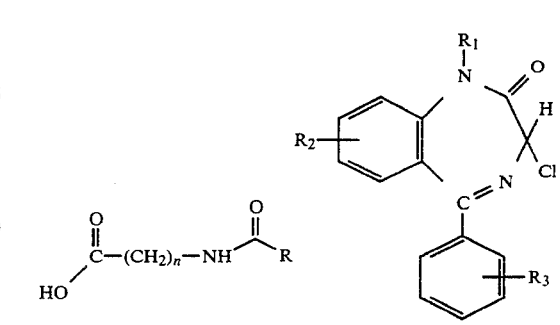

The preparation of C3—Cl substituted derivatives is described by T. Kovac et al., J. Med. Chem. 17, 766 (1974). In general formula (II), R and n have the same meaning as in general formula (I). In general formula (III) $R_1$, $R_2$, $R_3$ have the same meaning as in general formula (I).

The suitable base consists of an organic base selected from triethylamine, tributylamine, pyridine, 4-dimethyl amino-pyridine. The solvent can be selected between aprotic solvents such as acetonitrile, acetone, ethylacetate, etc. or the base itself can play the role of the solvent. The temperature which influences the speed of the reaction can be conveniently chosen between 20° C. and 100° C. depending also from the boiling point of the selected solvent.

An alternative method of synthesis of compounds of general formula (I) consists in reacting a C3-hydroxy compound of general formula (IV) with a compound of general formula (III) in the presence of a suitable condensing agent, in a suitable solvent.

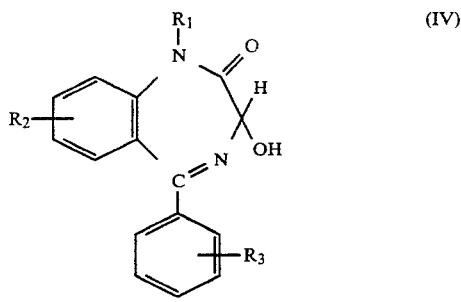

In formula (IV) $R_1$, $R_2$, $R_3$ have the same meaning as in formula (I). The preferred condensing agent is N,N'-dicyclohexylcarbodiimide in the presence of catalytic amounts of an organic base such as pyridine and 4-pyrrolidino-pyridine. The solvent consists of an aprotic solvent such as methylene chloride, benzene, toluene or tetrahydrofurane.

A third method of synthesis consists in reacting a compound of general formula (IV) with the acid chloride derived from general formula (III) in the presence of an at least equivalent amount of an organic base such as pyridine, substituted pyridine, triethylamine, in a water free aprotic solvent such as methylene chloride, acetone, ethylacetate, diethylether or the base itself playing the role of the solvent.

In order to illustrate the invention but without being limited thereto, the following examples of preparation are given.

EXAMPLE 1

A solution of 1.45 g (10 mmol) N-acetyl-γ-aminobutyric acid, 2.1 ml (15 mmol) triethylamine and 3.05 g (10 mmol) 3,7-dichloro-1,3-dihydro-5-phenyl-2H-1,4 benzodiazepine-2-one is stirred at room temperature during about 1 hour under nitrogen. The solvent is removed under vacuum and the residual solid is stirred in 30 ml cold water during 30 minutes under ice cooling. The formed slurry is filtered and the collected material is washed several times with water and with a small amount of cold acetone. Recrystallization of the crude product from 25 ml acetonitrile yields after drying 1.4 g analytically pure 3-(4-acetamido)butyryl-oxy-7-chloro-1,3-dihydro-5-phenyl-2H-1,4-benzodiazepine-2-one with a melting point 199°–201° C.

Analysis for $C_{21}H_{20}ClN_3O_4$: Calculated: C 60.95 H 4.87 N 10.15 Cl 8.57. Found: C 60.76 H 5.00 N 10.07 Cl 8.53.

EXAMPLE 2

A solution of 2.37 g (11.6 mmol) of N-tertiarybutyloxycarbonyl-γ-aminobutyric acid and 2.63 g (12.76 mmol) N,N'-dicyclohexyl-carbodiimide in dry methylene chloride was stirred at room temperature under nitrogen during 15 minutes. 172 mg (1.16 mmol) of 4-pyrrolidinopyridine and 2.22 g (7.73 mmol) 7-chloro-1,3-dihydro-3-hydroxy-5-phenyl-2H-1,4-benzodiazepine-2-one is then added. The mixture is stirred during 1 hour at 40° C. The mixture is then washed successively with water (3×100 ml), 5% acetic acid (2×100 ml), sat. NaHCO₃ (100 ml) water (100 ml). The organic phase is dried over anhydrous MgSO₄. Evaporation of the solvent to dryness leaves 4.06 g of an amorphous solid. This product was chromatographed in 1 g portions over 120 g silica gel (4.5×15 cm). The material was eluted with a 50:1 mixture of methylene chloride/methanol. Fractions containing impurities were combined and rechromatographed in the same way. After drying at 50° C./0.1 Torr, a total amount of 1.2 g amorphous, analytically pure 7-chloro-1,3-dihydro-5-phenyl-3-(4-tertiary-butoxycarbonylamino)butyryloxy-2H-1,4-benzodiazepine-2-one was obtained.

Analysis for $C_{24}H_{26}ClN_3O_5$: Calculated C 61.08 H 5.57 N 8.90 Cl 7.51. Found: C 60.91 H 5.60 N 8.78 Cl 7.53.

EXAMPLE 3

To a solution of 3.83 g (26.4 mmol) N-acetyl-γ-aminobutyric acid and 7.36 ml (52.8 mmol) triethylamine in 70 ml absolute acetonitrile was added 8.15 g (24 mmol) 3,7-dichloro-5-o-chlorophenyl-1,3-dihydro-2H-1,4-benzodiazepine-2-one.

After stirring during 20 minutes at room temperature under nitrogen the solvent was evaporated and the residue chromatographed on 170 g silicagel. Elution with an 11:1 mixture of methylene chloride/methanol yielded after evaporation of the solvents and crystallization from methylene chloride/diethylether an almost pure product. Recrystallization from ethylmethylketone yields 2.4 g of product. Recrystallization of the product obtained from the mother liquors yields additional 1.2 g of product. The combined crops (after drying at 70° C./0.2 Torr during 3 days) have a melting point 120°–121° C. Microanalysis shows that the obtained 3-(4-acetamido)butyryloxy-7-chloro-5-o-chlorophenyl-1,3-dihydro-2H-1,4-benzodiazepine-2-one crystallizes with half a molecule of solvent.

Analysis for $C_{21}H_{19}Cl_2N_3O_4.1/2C_4H_8O$: Calculated: C 57.03 H 4.78 N 8.67 Cl 14.63. Found: C 57.01 H 4.60 N 8.78 Cl 14.78.

EXAMPLE 4

To a solution of 3.13 g (21.56 mmol) N-acetyl-γ-aminobutyric acid and 4.1 ml (29.42 mmol) dry triethylamine in 60 ml dry acetonitrile is added 6.27 g (19.6 mmol)) of 3,7-dichloro-1,3-dihydro-1-methyl-5-phenyl-2H-1,4-benzodiazepine-2-one.

The solution is stirred under nitrogen and temperature is kept at 60° C. during 12 hours and successively at 80° C. for another 7 hours. The dark brown solution is concentrated to an oily residue which is filtered on 150 g silica gel. The fraction eluted with methylene chloride/methanol 15:1 are evaporated to dryness and the solid residue (4 g) is crystallized from methylene chloride/diethylether. A recrystallization from acetonitrile/diisopropylether yields after drying at 40° C./0.5 Torr during 90 hours 2.84 g of analytically pure 3-(4-acetamido)butyryloxy-7-chloro-1,3-dihydro-1-methyl-5-phenyl-2H-1,4-benzodiazepine-2-one m.p. 131°–132°.

Analysis for $C_{22}H_{22}ClN_3O_4$: Calculated: C 61.65 H 5.18 N 9.82 Cl 8.28. Found: C 61.81 H 5.09 N 10.02 Cl 8.26.

EXAMPLE 5

To a solution of 3.70 g (31.66 mmol) N-acetylglycine and 4.40 ml (31.66 mmol) triethylamine in 80 ml dry acetonitrile is added 12 g (31.66 mmol) solid 3,7-dichloro-1,3-dihydro-5-phenyl-2H-1,4-benzodiazepine-2-one. The resulting suspension is stirred at room temperature under nitrogen. An additional amount of 2.2 ml (15.83 mmol) triethylamine is added after 30 and 120 minutes respectively.

After 3 hours the solvent is completely removed in vacuo, the residue dissolved in 25 ml methylenechloride/methanol 9:1 and crystallized by stirring the sealed solution for 1 hour at room temperature. Recrystallization from 27 ml methyl-ethylketone yields 6.35 g analytically pure 3-acetamido-acetoxy-7-chloro-1,3-dihydro-5-phenyl-2H-1,4-benzodiazepine-2-one, melting at 210°–211° C.

Analysis for $C_{19}H_{16}ClN_3O_4$: Calculated: C 59.15 H 4.18 N 10.89 Cl 9.19. Found: C 58.96 H 4.33 N 10.73 Cl 9.05.

EXAMPLE 6

A solution of 4.65 g (32.06 mmol) N-acetyl-γ-aminobutyric acid, 4.46 ml (32.00 mmol) triethylamine and 10.3 g (29.15 mmol) 7-chloro-5-o-chlorophenyl-1,3-dihydro-3-hydroxy-2H-1,4-benzodiazepine-2-one in 90 ml dry acetonitrile was refluxed during 125 hours. The dark brown mixture was evaporated and the residue chromatographed on 450 g silica gel in ether/methanol 9:1 and subsequently on 200 g florisil in methylene chloride/ethanol 25:1. The obtained material was dissolved in acetone, filtered, the filtrate evaporated and the residue dried at 50°/0.5 Torr during 50 hours to give 3.5 g amorphous 3-(4-acetamido)-butyryloxy-7-chloro-5-o-chlorophenyl-1,3-dihydro-1-methyl-2H-1,4-benzodiazepine-2-one.

Analysis for $C_{22}H_{21}Cl_2N_3O_4$:

Calculated: C 57.16 H 4.58 N 9.08 Cl 15.33. Found: C 57.38 H 4.92 N 8.87 Cl 14.25.

Toxicity tests

The compounds of the invention have a low toxicity as shown in Table 1.

TABLE 1

| Compound | $LD_{50}$ mice p. os in mg/kg |
|---|---|
| Oxazepam | >1500 |
| Example 1 | 1500 |
| Example 2 | >1500 |
| Example 3 | 1200 |
| Example 4 | 1000 |
| Example 5 | 1400 |
| Example 6 | >1000 |

Pharmacological tests

The pharmacologic activity of the compounds of the invention has been assessed by the following classical tests which are known to indicate useful therapeutic activities:

Anti-pentylenetetrazol (L. O. Randall, W. Schallek, G. A. Heise, E. F. Keith and R. Bagdon: J. Pharmacol. Exp. Therapeutics, 129, 163–171, 1960).

ECS (E. A. Swinyard, W. C. Brown and L. S. Goodman: J. Pharmacol. Exp. Therapeutics, 106, 319–330, 1952.)

Analgesic (N. B. Eddy and D. Leimbach: J. Pharmacol. Exp. Therapeutics, 107, 385–393, 1953.)

Miorelaxation (N. W. Dunham and T. S. Miya: J. Am. Pharm. Ass., 46, No. 3, 208–209, 1957.)

Spontaneous Motor Activity (W. J. Kinnard and C. J. Carr: J. Pharmacol. Exp. Therapeutics, 121, 354–361, 1957.)

These activities are shown in Table 2.

TABLE 2

| | Main neuropharmacological effects of substituted benzodiazepine in oral administration (mg/kg) | | | | | | |
|---|---|---|---|---|---|---|---|
| | Anti-pentylenetetrazol[a] | | Anti-ECS[b] | | | | Spontaneous Motor |
| | Death | Convulsions | Death | Convulsions | Analgesic[c] | Miorelaxation[d] | Activity |
| Compound | $DE_{50}$ | $DE_{50}$ | $DE_{50}$ | $DE_{50}$ | $DE_{50}^{(x)}$ | $DE_{50}^{(xx)}$ | $DE_{50}^{(xxx)}$ |
| Example 1 | 4 | 7 | 0.22 | 38 | 26 | 6.5 | 9 |
| Example 2 | 7 | 14 | 1 | 60 | 42 | 16 | 2.6 |
| Example 3 | 0.15 | 2.6 | 0.02 | 4.6 | 42 | 4.2 | 0.18 |
| Example 4 | 2.2 | 5 | 0.7 | 4 | 30 | 19 | 1.9 |
| Example 5 | 1.5 | 6 | 0.32 | 12 | 34 | 15 | 0.7 |
| Example 6 | 0.16 | 0.20 | 0.032 | 5.5 | 19[c'] | 2[d'] | 1.9 |
| Oxazepam | 5.5 | 20 | 4 | 40 | 28 | 25 | 4.2 |

[a]30 minutes before pentylenetetrazol treatment 130 mg/kg s.c.
[b]60 minutes before ECS.
[c]at 240 minutes after drug treatment.
[d]at 120 minutes after drug treatment.
[d']at 60 minutes after drug treatment.
[e]measured in 30 minutes period starting 30 minutes after drug treatment.
[c']at 60 minutes after drug treatment.
[(x)]Prolongs reaction time 50 percent of control group in 50 percent of treated animals.
[(xx)]Reduces "falling time" 50 percent of control group in 50 percent of treated animals.
[(xxx)]Reduces movements counts 50 percent of control activity in group of 4 animals: 5 groups/dose.

Examination of the data of table 2 show that the compounds of the invention possess at low doses in the range of 0.5 to 40 mg/kg pronounced activities as anticonvulsant, analgesics, myorelaxants, sedatives, hypnotics, anxiolytics. These properties together with their low level of toxicity make them particularly useful for the treatment of human and animal diseases such as epilexy, pain, anxiety, agressiveness, insomnia, muscular pain due to contraction.

More generally the compounds of the invention possess one or more useful pharmacological actions on the central nervous system of mammals.

They can be included in pharmaceutical compositions as active agents useful for the medical treatment of the above mentioned diseases, in the field of psychosomatic and psychiatric medicine.

The compounds of the invention can be administered orally, parenterally or rectally in the conventional dosage forms such as tablets, capsules, solutions, suspensions, injectables, suppositories, together with pharmaceutically compatible, non toxic diluents and eccipients.

I claim:

1. A 1,4-benzodiazepine compound having the formula

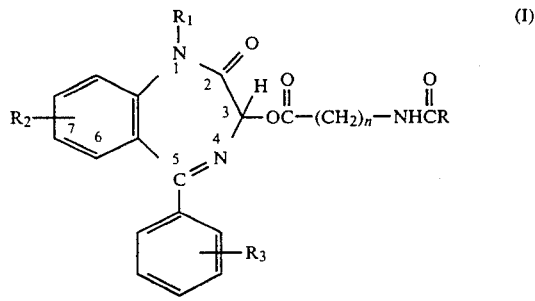

(I)

wherein R is selected from the group comprising a lower alkyl with up to 5 carbon atoms, alkoxy with up to 4 carbon atoms, branched or straight chain; $R_1$ is selected from the group comprising H, $-CH_3$, $-CH_2CH_2N(C_2H_5)_2$; $R_2$ and $R_3$ are each individually selected from the group comprising H, Br, Cl, F trifluoromethyl, $NO_2$; n is a whole integer from 1 to 5.

2. A compound according to claim 1 in which $R_2$ is located in position 7 of the ring system.

3. A compound according to claim 1 in which $R_1$ is chlorine.

4. A compound according to claim 1 in which $R_3$ is located in position -ortho-.

5. A compound according to claim 1 in which $R_3$ is chlorine.

6. A compound according to claim 1 in which R is —CH₃.

7. A compound according to claim 1 in which R is tertiary butyloxy.

8. A compound according to claim 1 in which n is 3.

9. A compound according to claim 1 in which n is 1.

10. 3-(4-acetamido)butyryloxy-7-chloro-1,3-dihydro-5-phenyl-2H-1,4-benzodiazepine-2-one.

11. 3-(4-tertiarybutyloxycarbonylamino)butyryloxy-7-chloro-1,3-dihydro-5-phenyl-2H-1,4-benzodiazepine-2-one.

12. 3-(4-acetamido)butyryloxy-7-chloro-5-o-chlorophenyl-1,3-dihydro-2H-1,4-benzodiazepine-2-one.

13. 3-(4-acetamido)butyryloxy-7-chloro-1,3-dihydro-1-methyl-5-phenyl-2H-1,4-benzodiazepine-2-one.

14. 3-acetamido-acetoxy-7-chloro-1,3-dihydro-5-phenyl-2H-1,4-benzodiazepine-2-one.

15. 3-(4-acetamido)-butyryloxy-7-chloro-5-o-chlorophenyl-1,3-dihydro-1-methyl-2H-1,4-benzodiazepine-2-one.

16. A composition for use in psychosomatic and psychiatric medicine, comprising as a sedative-hypnotic, anxyolytic, anticonvulsivant and analgesic agent, a therapeutically effective amount of 1,4-benzodiazepine compound having the formula as defined in claim 1, and pharmaceutically compatible diluents and eccipients.

17. A method for the treatment of psychosomatic and psychic disturbances comprising administering an effective amount of a 1,4-benzodiazepine compound having the formula as defined in claim 1.

* * * * *